United States Patent
Bhatnagar et al.

(10) Patent No.: US 6,864,267 B2
(45) Date of Patent: *Mar. 8, 2005

(54) CALCILYTIC COMPOUNDS

(75) Inventors: Pradip K. Bhatnagar, King of Prussia, PA (US); James F. Callahan, Collegeville, PA (US); Amparo M. Lago, Collegeville, PA (US)

(73) Assignee: SmithKline Beecham Corporation, Philadelphia, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 10/333,096

(22) PCT Filed: Jul. 16, 2001

(86) PCT No.: PCT/US01/22267

§ 371 (c)(1),
(2), (4) Date: Jan. 15, 2003

(87) PCT Pub. No.: WO02/07673

PCT Pub. Date: Jan. 31, 2002

(65) Prior Publication Data

US 2003/0212110 A1 Nov. 13, 2003

(51) Int. Cl.[7] .................. A61K 31/4436; C07D 409/02

(52) U.S. Cl. .................... 514/336; 546/280.4; 546/288; 546/315; 546/326; 514/344; 514/354

(58) Field of Search .................. 514/336, 344, 514/354; 546/280.4, 288, 315, 326

(56) References Cited

U.S. PATENT DOCUMENTS

| | | |
|---|---|---|
| 5,158,956 A | 10/1992 | Gidda et al. |
| 5,258,379 A | 11/1993 | Gidda et al. |
| 6,417,215 B1 * | 7/2002 | Lago .......................... 514/381 |

FOREIGN PATENT DOCUMENTS

| | | | |
|---|---|---|---|
| WO | 00/45816 | * 8/2000 | ................. 514/381 |

* cited by examiner

Primary Examiner—Charanjit S. Aulakh
(74) Attorney, Agent, or Firm—Soma G. Simon; Mary E. McCarthy; Charles M. Kinzig

(57) ABSTRACT

Novel calcilytic compounds and methods of using them are provided.

4 Claims, No Drawings

# CALCILYTIC COMPOUNDS

FIELD OF INVENTION

The present invention relates to novel calcilytic compounds, pharmaceutical compositions containing these compounds and their use as calcium receptor antagonists.

In mammals, extracellular $Ca^{2+}$ is under rigid homeostatic control and regulates various processes such as blood clotting, nerve and muscle excitability, and proper bone formation. Extracellular $Ca^{2+}$ inhibits the secretion of parathyroid hormone ("PTH") from parathyroid cells, inhibits bone resorption by osteoclasts, and stimulates secretion of calcitonin from C-cells. Calcium receptor proteins enable certain specialized cells to respond to changes in extracellular $Ca^{2+}$ concentration.

PTH is the principal endocrine factor regulating $Ca^{2+}$ homeostasis in the blood and extracellular fluids. PTH, by acting on bone and kidney cells, increases the level of $Ca^{2+}$ in the blood. This increase in extracellular $Ca^{2+}$ then acts as a negative feedback signal, depressing PTH secretion. The reciprocal relationship between extracellular $Ca^{2+}$ and PTH secretion forms an important mechanism maintaining bodily $Ca^{2+}$ homeostasis.

Extracellular $Ca^{2+}$ acts directly on parathyroid cells to regulate PTH secretion. The existence of a parathyroid cell surface protein which detects changes in extracellular $Ca^{2+}$ has been confirmed. See Brown et al., Nature 366:574, 1993. In parathyroid cells, this protein, the calcium receptor, acts as a receptor for extracellular $Ca^{2+}$, detects changes in the ion concentration of extracellular $Ca^{2+}$, and initiates a functional cellular response, PTH secretion.

Extracellular $Ca^{2+}$ influences various cell functions, reviewed in Nemeth et al., Cell Calcium 11:319, 1990. For example, extracellular $Ca^{2+}$ plays a role in parafollicular (C-cells) and parathyroid cells. See Nemeth, Cell Calcium 11:323, 1990. The role of extracellular $Ca^{2+}$ on bone osteoclasts has also been studied. See Zaidi, Bioscience Reports 10:493, 1990.

Various compounds are known to mimic the effects of extra-cellular $Ca^{2+}$ on a calcium receptor molecule. Calcilytics are compounds able to inhibit calcium receptor activity, thereby causing a decrease in one or more calcium receptor activities evoked by extracellular $Ca^{2+}$. Calcilytics are useful as lead molecules in the discovery, development, design, modification and/or construction of useful calcium modulators which are active at $Ca^{2+}$ receptors. Such calcilytics are useful in the treatment of various disease states characterized by abnormal levels of one or more components, e.g., polypeptides such as hormones, enzymes or growth factors, the expression and/or secretion of which is regulated or affected by activity at one or more $Ca^{2+}$ receptors. Target diseases or disorders for calcilytic compounds include diseases involving abnormal bone and mineral homeostasis.

Abnormal calcium homeostasis is characterized by one or more of the following activities: an abnormal increase or decrease in serum calcium; an abnormal increase or decrease in urinary excretion of calcium; an abnormal increase or decrease in bone calcium levels (for example, as assessed by bone mineral density measurements); an abnormal absorption of dietary calcium; an abnormal increase or decrease in the production and/or release of messengers which affect serum calcium levels such as PTH and calcitonin; and an abnormal change in the response elicited by messengers which affect serum calcium levels.

Thus, calcium receptor antagonists offer a unique approach towards the pharmacotherapy of diseases associated with abnormal bone or mineral homeostasis, such as hypoparathyroidism, osteosarcoma, periodontal disease, fracture healing, osteoarthritis, rheumatoid arthritis, Paget's disease, humoral hypercalcemia associated with malignancy and fracture healing, and osteoporosis.

SUMMARY OF THE INVENTION

The present invention comprises novel calcium receptor antagonists represented by Formula (I) hereinbelow and their use as calcium receptor antagonists in the treatment of a variety of diseases associated with abnormal bone or mineral homeostasis, including but not limited to hypoparathyroidism, osteosarcoma, periodontal disease, fracture healing, osteoarthritis, rheumatoid arthritis, Paget's disease, humoral hypercalcemia associated with malignancy and fracture healing, and osteoporosis.

The present invention further provides a method for antagonizing calcium receptors in an animal, including humans, which comprises administering to an animal in need thereof an effective amount of a compound of Formula (I), indicated hereinbelow.

The present invention further provides a method for increasing serum parathyroid levels in an animal, including humans, which comprises administering to an animal in need thereof an effective amount of a compound of Formula (I), indicated herein below.

DETAILED DESCRIPTION OF THE INVENTION

The compounds of the present invention are selected from Formula (I) herein below:

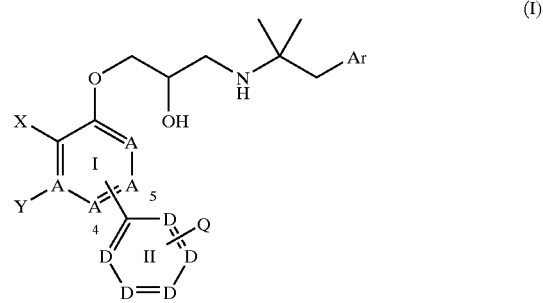

wherein:
A represents C or N with one or two N in ring I;
D represents C or N with one or two N in the ring II that is attached at position 4 or 5 to ring I as indicated;
X is selected from the group consisting of CN, $NO_2$, Cl, F, and H;
Y is selected when A is C from the group consisting of Cl, F, Br, I and H;
Q is selected when D is C from the group consisting of H, $R_1$, $SO_2R_1'$,
$R_1C(O)OR'_1$, tetrazole, $CH_2OH$, COH, $SO_2NR_1'R_1''$, $C(O)NR_1'R_1''$, and
$NR_1SO_2R_1'$, wherein $R_1$ is independently selected from the group consisting of bond, hydrogen, $C_{1-4}$ alkyl, and optionally substituted alkyl;
$R_1'$, and $R_1''$ are independently selected from the group consisting of hydrogen, $C_{1-4}$ alkyl, and optionally substituted alkyl, or $R_1'$, and $R_1''$ together form a 3 to 7 membered optionally substituted heterocyclic ring; and Ar is phenyl or naphthyl, unsubstituted or substituted, heteroaryl or fused heteroaryl, such that the hetero-ring may contain N, O or S and may be aromatic, dihydro or tetrahydro, unsubstituted or substituted.

As used herein, "alkyl" refers to an optionally substituted hydrocarbon group joined by single carbon-carbon bonds and having 1–20 carbon atoms joined together. The alkyl hydrocarbon group may be linear, branched or cyclic, saturated or unsaturated. Preferably, substituents on optionally substituted alkyl are selected from the group consisting of aryl, $CO_2R$, $CO_2NHR$, OH, OR, CO, $NH_2$, halo, $CF_3$, $OCF_3$ and $NO_2$, wherein R represents H, $C_{1-4}$ alkyl $C_{3-6}$ cycloalkyl, $C_{2-5}$ alkenyl, $C_{2-5}$ alkynyl, heterocycloalkyl, aryl or aryl $C_{1-4}$ alkyl; Additional substituents are selected from F, Cl, Br, I, N, S and O. Preferably, no more than three substituents are present. More preferably, the alkyl has 1–12 carbon atoms and is unsubstituted. Preferably, the alkyl group is linear.

As used herein "cycloalkyl" refers to optionally substituted 3–7 membered carbocyclic rings wherein any substituents are selected from the group consisting of, F, Cl, Br, I, $N(R_4)_2$, $SR_4$ and $OR_4$, unless otherwise indicated.

As used herein, "aryl" refers to an optionally substituted aromatic group with at least one ring having a conjugated pi-electron system, containing up to two conjugated or fused ring systems. Aryl includes carbocyclic aryl, and biaryl groups, all of which may be optionally substituted. Preferred aryl include phenyl and naphthyl. More preferred aryl include phenyl. Preferred substituents are selected from the group consisting of halogen, $C_{1-4}$ alkyl $OCF_3$, $CF_3$, OMe, CN, $OSO_2$ R and $NO_2$, wherein R represents $C_{1-4}$ alkyl or $C_{3-6}$ cycloalkyl.

As used herein, "alkenyl" refers to an optionally substituted hydrocarbon group containing at least one carbon-carbon double bond and containing up to 5 carbon atoms joined together. The alkenyl hydrocarbon chain may be straight, branched or cyclic. Any substituents are selected from the group consisting of halogen, $C_{1-4}$ alkyl, $OCF_3$, $CF_3$, OMe, CN, $OSO_2$ R and $NO_2$, wherein R represents $C_{1-4}$ alkyl or $C_{3-6}$ cycloalkyl.

As used herein, "alkynyl" refers to an optionally substituted hydrocarbon group containing at least one carbon-carbon triple bond between the carbon atoms and containing up to 5 carbon atoms joined together. The alkynyl hydrocarbon group may be straight-chained, branched or cyclic. Any substituents are selected from the group consisting of halogen, $C_{1-4}$ alkyl, $OCF_3$, $CF_3$, OMe, CN, $OSO_2$ R and $NO_2$, wherein R represents $C_{1-4}$ alkyl or $C_{3-6}$ cycloalkyl.

The compounds of the present invention may contain one or more asymmetric carbon atoms and may exist in racemic and optically active forms. All of these compounds and diastereomers are contemplated to be within the scope of the present invention.

Preferred compounds of the present inventions include:

N-[(2R)-Hydroxy-3-[[2-cyano-5-[[5-ethylcarboxyl]-3-pyridyl]phenoxy]propyl]]-1,1-dimethyl-2-(5-chlorothienyl)ethylamine;

N-[(2R)-Hydroxy-3-[[2-cyano-5-[[5-carboxyl]-3-pyridyl]phenoxy]propyl]]-1,1-dimethyl-2-(5-chlorothienyl)ethylamine;

N-[(2R)-Hydroxy-3-[[2-cyano-5-[[5-ethylcarboxyl]-3-pyridyl]phenoxy]propyl]]-1,1-dimethyl-2-(indan-2-yl)ethylamine;

N-[(2R)-Hydroxy-3-[[2-cyano-5-[[5-carboxyl]-3-pyridyl]phenoxy]propyl]]-1,1-dimethyl-2-(indan-2-yl)ethylamine;

N-[(2R)-Hydroxy-3-[[2-cyano-5-[[5-ethylcarboxyl]-3-pyridyl]phenoxy]propyl]]-1,1-dimethyl-4-(methoxyphenyl)ethylamine;

N-[(2R)-Hydroxy-3-[[2-cyano-5-[[5-carboxyl]-3-pyridyl]phenoxy]propyl]]-1,1-dimethyl-4-(methoxyphenyl)ethylamine;

N-[(2R)-Hydroxy-3-[[2-cyano-5-[[3-ethylcarboxyl]-2-pyridyl]phenoxy]propyl]]-1,1-dimethyl-2-(5-chlorothienyl)ethylamine;

N-[(2R)-Hydroxy-3-[[2-cyano-5-[[3-carboxyl]-2-pyridyl]phenoxy]propyl]]-1,1-dimethyl-2-(5-chlorothienyl)ethylamine;

N-[(2R)-Hydroxy-3-[[2-cyano-5-[[3-ethylcarboxyl]-2-pyridyl]phenoxy]propyl]]-1,1-dimethyl-2-(indan-2-yl)ethylamine;

N-[(1,1-Hydroxy-3-[[2-cyano-5-[[3-carboxyl]-2-pyridyl]phenoxy]propyl]]-1,1-dimethyl-2-(indan-2-yl)ethylamine;

N-[(2R)-Hydroxy-3-[[2-cyano-5-[[3-ethylcarboxyl]-2-pyridyl]phenoxy]propyl]]-1,1-dimethyl-4-(methoxyphenyl)ethylamine;

N-[(2R)-Hydroxy-3-[[2-cyano-5-[[3-carboxyl]-2-pyridyl]phenoxy]propyl]]-1,1-dimethyl-4-(methoxyphenyl)ethylamine;

N-[(2R)-Hydroxy-3-[[2-cyano-4-[[4-ethylcarboxyl]phenyl]-3-pyridyloxy]propyl]]-1,1-dimethyl-2-(5-chlorothienyl)ethylamine;

N-[(2R)-Hydroxy-3-[[2-cyano-4-[[4-carboxyl]phenyl]-3-pyridyloxy]propyl]]-1,1-dimethyl-2-(5-chlorothienyl)ethylamine;

N-[(2R)-Hydroxy-3-[[2-cyano-4-[[4-ethylcarboxyl]phenyl]-3-pyridyloxy]propyl]]-1,1-dimethyl-2-(indan-2-yl)ethylamine;

N-[(2R)-Hydroxy-3-[[2-cyano-4-[[4-carboxyl]phenyl]-3-pyridyloxy]]-1,1-dimethyl-2-(indan-2-yl)ethylamine;

N-[(2R)-Hydroxy-3-[[2-cyano-4-[[4-ethylcarboxyl]phenyl]-3-pyridyloxy]propyl]]-1,1-dimethyl-4-(methoxyphenyl)ethylamine; and N-[(2R)-Hydroxy-3-[[2-cyano-4-[[4-carboxyl]phenyl]-3-pyridyloxy]propyl]]-1,1-dimethyl-4-(methoxyphenyl)ethylamine.

Pharmaceutically acceptable salts are non-toxic salts in the amounts and concentrations at which they are administered.

Pharmaceutically acceptable salts include acid addition salts such as those containing sulfate, hydrochloride, fumarate, maleate, phosphate, sulfamate, acetate, citrate, lactate, tartrate, methanesulfonate, ethanesulfonate, benzenesulfonate, p-toluenesulfonate, cyclohexylsulfamate and quinate. A preferred salt is a hydrochloride. Pharmaceutically acceptable salts can be obtained from acids such as hydrochloric acid, maleic acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, fumaric acid, and quinic acid.

Pharmaceutically acceptable salts also include basic addition salts such as those containing benzathine, chloroprocaine, choline, diethanolamine, ethylenediamine, meglumine, procaine, aluminum, calcium, lithium, magnesium, potassium, sodium, ammonium, alkylamine, and zinc, when acidic functional groups, such as carboxylic acid or phenol are present.

The present invention provides compounds of Formula (I) above which can be prepared using standard techniques. An overall strategy for preparing preferred compounds described herein can be carried out as described in this section. The examples which follow illustrate the synthesis of specific compounds. Using the protocols described herein as a model, one of ordinary skill in the art can readily produce other compounds of the present invention.

All reagents and solvents were obtained from commercial vendors. Starting materials were synthesized using standard techniques and procedures.
Scheme 1
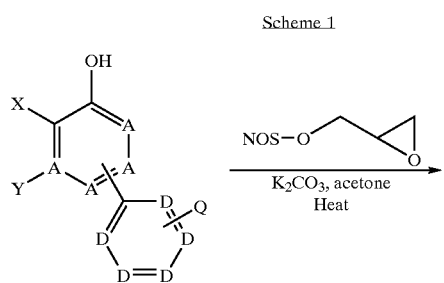
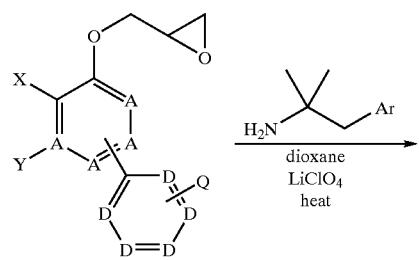
Scheme 2
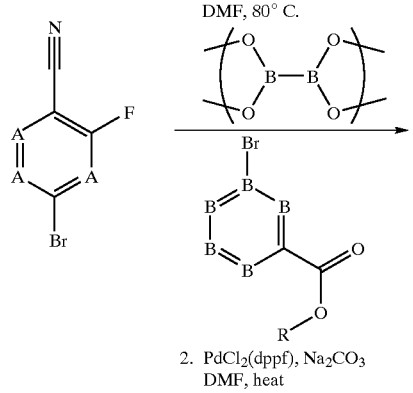
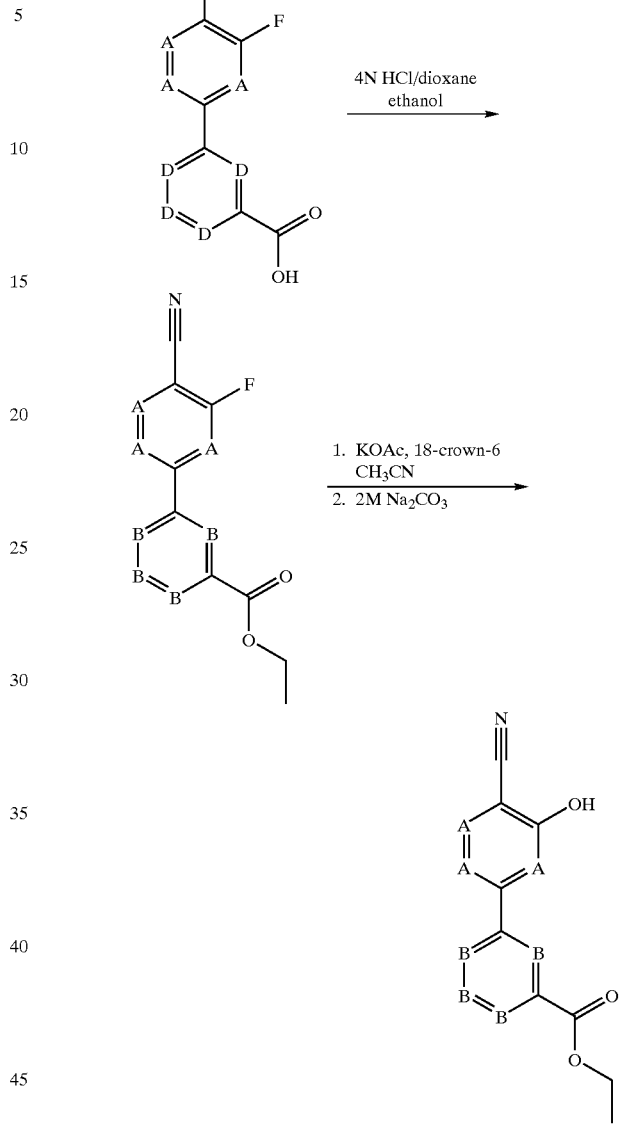
Scheme 3
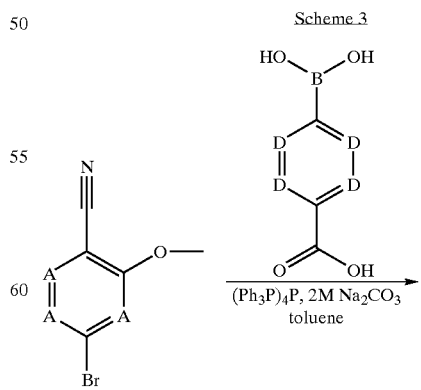

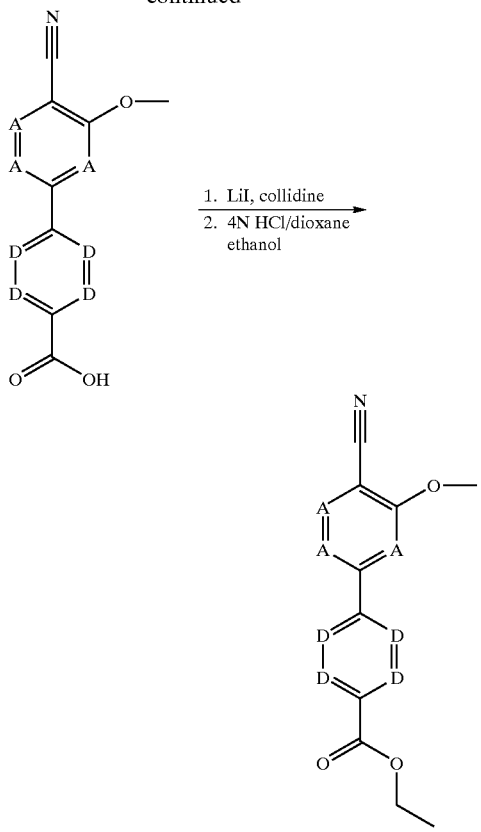

A general procedure used to synthesize many of the compounds can be carried out as described in Scheme 1, above: A solution of biaryl alcohol in acetone was treated with an appropriate base such as $K_2CO_3$, heated for 15 min. R-glycidyl nosylate was added and the reaction continued overnight to give the corresponding glycidyl ether (Scheme 1). A solution of the substituted glycidyl ether and excess amine (e.g., 1,1-dimethyl-2-(4-methyloxyphenyl)ethylamine) in absolute ethanol, acetonitrile, THF, dioxane or any other similar solvent in the presence of a suitable catalyst such as $LiClO_4$ is stirred overnight at reflux.

The product is purified by chromatography. Hydrochloride salts are prepared by treatment of the corresponding free base with HCl either in gas phase or 4M dioxane solution, or any other standard method. Methods to prepare the biarylphenol are outlined in Schemes 2 and 3.

A 2-fluoro-4-bromobenzonitrile in DMF is treated with boronate, potassium acetate and catalytic $PdCl_2(dppf)$ at 80° C. After the aryl bromide is consumed (about 2 h), the reaction is cooled to room temperature and treated with an aryl acid, 2 M sodium carbonate and additional palladium catalysis and then heated for 18 h to give the fluorine substituted biaryl product.

The fluorine is displaced with potassium acetate in acetonitrile in the presence of 18-crown-6 to give the corresponding phenol (see Scheme 2). Alternatively, a 2-methoxy-4-bromobenzonitrile can be coupled to a boronic acid substituted arylcarboxylic acid using a catalytic amount tetrakistriphenylphosphine palladium in a mixture of toluene and 2M sodium carbonate to give a biarylmethyl ether. Deprotection of the methyl ether (e.g., lithium iodide, collidine) followed by esterification gives the corresponding biarylphenol (Scheme 3).

In order to use a compound of Formula (I) or a pharmaceutically acceptable salt thereof for the treatment of humans and other mammals, it is normally formulated in accordance with standard pharmaceutical practice as a pharmaceutical composition.

The calcilytic compounds can be administered by different routes including intravenous, intraperitoneal, subcutaneous, intramuscular, oral, topical (transdermal), or transmucosal administration. For systemic administration, oral administration is preferred. For oral administration, for example, the compounds can be formulated into conventional oral dosage forms such as capsules, tablets, and liquid preparations such as syrups, elixirs, and concentrated drops.

Alternatively, injection (parenteral administration) may be used, e.g., intramuscular, intravenous, intraperitoneal, and subcutaneous. For injection, the compounds of the invention are formulated in liquid solutions, preferably, in physiologically compatible buffers or solutions, such as saline solution, Hank's solution, or Ringer's solution. In addition, the compounds may be formulated in solid form and redissolved or suspended immediately prior to use. Lyophilized forms can also be produced.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, bile salts and fusidic acid derivatives. In addition, detergents may be used to facilitate permeation. Transmucosal administration, for example, may be through nasal sprays, rectal suppositories, or vaginal suppositories.

For topical administration, the compounds of the invention can be formulated into ointments, salves, gels, or creams, as is generally known in the art.

The amounts of various calcilytic compounds to be administered can be determined by standard procedures taking into account factors such as the compound $IC_{50}$, $EC_{50}$, the biological half-life of the compound, the age, size and weight of the patient, and the disease or disorder associated with the patient. The importance of these and other factors to be considered are known to those of ordinary skill in the art.

Amounts administered also depend on the routes of administration and the degree of oral bioavailability. For example, for compounds with low oral bioavailability, relatively higher doses will have to be administered.

Preferably the composition is in unit dosage form. For oral application, for example, a tablet, or capsule may be administered, for nasal application, a metered aerosol dose may be administered, for transdermal application, a topical formulation or patch may be administered and for transmucosal delivery, a buccal patch may be administered. In each case, dosing is such that the patient may administer a single dose.

Each dosage unit for oral administration contains suitably from 0.01 to 500 mg/Kg, and preferably from 0.1 to 50 mg/Kg, of a compound of Formula (I) or a pharmaceutically acceptable salt thereof, calculated as the free base. The daily dosage for parenteral, nasal, oral inhalation, transmucosal or transdermal routes contains suitably from 0.01 mg to 100 mg/Kg, of a compound of Formula(I). A topical formulation contains suitably 0.01 to 5.0% of a compound of Formula (I). The active ingredient may be administered, for example, from 1 to 6 times per day, preferably once, sufficient to exhibit the desired activity, as is readily apparent to one skilled in the art.

As used herein, "treatment" of a disease includes, but is not limited to prevention, retardation and prophylaxis of the disease.

Diseases and disorders which might be treated or prevented, based upon the affected cells, include bone and mineral-related diseases or disorders; hypoparathyroidism; those of the central nervous system such as seizures, stroke, head trauma, spinal cord injury, hypoxia-induced nerve cell damage, such as occurs in cardiac arrest or neonatal distress, epilepsy, neurodegenerative diseases such as Alzheimer's disease, Huntington's disease and Parkinson's disease, dementia, muscle tension, depression, anxiety, panic disorder, obsessive-compulsive disorder, post-traumatic stress disorder, schizophrenia, neuroleptic malignant syndrome, and Tourette's syndrome; diseases involving excess water reabsorption by the kidney, such as syndrome of inappropriate ADH secretion (SIADH), cirrhosis, congestive heart failure, and nephrosis; hypertension; preventing and/or decreasing renal toxicity from cationic antibiotics (e.g., aminoglycoside antibiotics); gut motility disorders such as diarrhea and spastic colon; GI ulcer diseases; GI diseases with excessive calcium absorption such as sarcoidosis; autoimmune diseases and organ transplant rejection; squamous cell carcinoma; and pancreatitis.

In a preferred embodiment of the present invention, the present compounds are used to increase serum parathyroid hormone ("PTH") levels. Increasing serum PTH levels can be helpful in treating diseases such as hypoparathyroidism, osteosarcoma, periodontal disease, fracture, osteoarthritis, rheumatoid arthritis, Paget's disease, humoral hypercalcemia malignancy and osteoporosis.

In a preferred embodiment of the present invention, the present compounds are co-administered with an anti-resorptive agent. Such agents include, but are not limited estrogen, 1, 25 $(OH)_2$ vitamin D3, calcitonin, selective estrogen receptor modulators, vitronectin receptor antagonists, V-H+-ATPase inhibitors, src SH2 antagonists, bisphosphonates and cathepsin K inhibitors.

Another aspect of the present invention describes a method of treating a patient comprising administering to the patient an amount of a present compound sufficient to increase the serum PTH level. Preferably, the method is carried out by administering an amount of the compound effective to cause an increase in duration and/or quantity of serum PTH level sufficient to have a therapeutic effect.

In various embodiments, the compound administered to a patient causes an increase in serum PTH having a duration of up to one hour, about one to about twenty-four hours, about one to about twelve hours, about one to about six hours, about one to about five hours, about one to about four hours, about two to about five hours, about two to about four hours, or about three to about six hours.

In an alternattive embodiment of the present invention, the compound administered to a patient causes an increase in serum PTH having a duration of more than about twenty four hours provided that it is co-administered with an anti resorptive agent.

In additional different embodiments, the compound administered to a patient causes an increase in serum PTH of up to two fold, two to five fold, five to ten fold, and at least 10 fold, greater than peak serum PTH in the patient. The peak serum level is measured with respect to a patient not undergoing treatment.

Composition of Formula (I) and their pharmaceutically acceptable salts which are active when given orally can be formulated as syrups, tablets, capsules and lozenges. A syrup formulation will generally consist of a suspension or solution of the compound or salt in a liquid carrier for example, ethanol, peanut oil, olive oil, glycerine or water with a flavoring or coloring agent. Where the composition is in the form of a tablet, any pharmaceutical carrier routinely used for preparing solid formulations may be used. Examples of such carriers include magnesium stearate, terra alba, talc, gelatin, acacia, stearic acid, starch, lactose and sucrose. Where the composition is in the form of a capsule, any routine encapsulation is suitable, for example using the aforementioned carriers in a hard gelatin capsule shell. Where the composition is in the form of a soft gelatin shell capsule any pharmaceutical carrier routinely used for preparing dispersions or suspensions may be considered, for example aqueous gums, celluloses, silicates or oils, and are incorporated in a soft gelatin capsule shell.

Typical parenteral compositions consist of a solution or suspension of a compound or salt in a sterile aqueous or non-aqueous carrier optionally containing a parenterally acceptable oil, for example polyethylene glycol, polyvinylpyrrolidone, lecithin, arachis oil or sesame oil.

Typical compositions for inhalation are in the form of a solution, suspension or emulsion that may be administered as a dry powder or in the form of an aerosol using a conventional propellant such as dichlorodifluoromethane or trichlorofluoromethane.

A typical suppository formulation comprises a compound of Formula (I) or a pharmaceutically acceptable salt thereof which is active when administered in this way, with a binding and/or lubricating agent, for example polymeric glycols, gelatins, cocoa-butter or other low melting vegetable waxes or fats or their synthetic analogs.

Typical dermal and transdermal formulations comprise a conventional aqueous or non-aqueous vehicle, for example a cream, ointment, lotion or paste or are in the form of a medicated plaster, patch or membrane.

Preferably the composition is in unit dosage form, for example a tablet, capsule or metered aerosol dose, so that the patient may administer a single dose.

No unacceptable toxological effects are expected when compounds of the present invention are administered in accordance with the present invention.

The biological activity of the compounds of Formula (I) are demonstrated by the following tests:

(I) Calcium Receptor Inhibitor Assay

Calcilytic activity was measured by determining the $IC_{50}$ of the test compound for blocking increases of intracellular $Ca^{2+}$ elicited by extracellular $Ca^{2+}$ in HEK 293 4.0–7 cells stably expressing the human calcium receptor. HEK 293 4.0–7 cells were constructed as described by Rogers et al., J. Bone Miner. Res. 10 Suppl. 1:S483, 1995 (hereby incorporated by reference herein). Intracellular $Ca^{2+}$ increases were elicited by increasing extracellular $Ca^{2+}$ from 1 to 1.75 mM. Intracellular $Ca^{2+}$ was measured using fluo-3, a fluorescent calcium indicator.

The procedure was as follows:

1. Cells were maintained in T-150 flasks in selection media (DMEM supplemented with 10% fetal bovine serum and 200 ug/mL hygromycin B), under 5% $CO_2$:95% air at 37° C. and were grown up to 90% confluency.

2. The medium was decanted and the cell monolayer was washed twice with phosphate-buffered saline (PBS) kept at 37° C. After the second wash, 6 mL of $0.0_2$% EDTA in PBS was added and incubated for 4 minutes at 37° C. Following the incubation, cells were dispersed by gentle agitation.

3. Cells from 2 or 3 flasks were pooled and pelleted (100×g). The cellular pellet was resuspended in 10–15 mL of SPF-PCB+ and pelleted again by centrifugation. This washing was done twice.

Sulfate- and phosphate-free parathyroid cell buffer (SPF-PCB) contains 20 mM Na-Hepes, pH 7.4, 126 mM NaCl, 5 mM KCl, and 1 mM $MgCl_2$. SPF-PCB was made up and stored at 4° C. On the day of use, SPF-PCB was supplemented with 1 mg/mL of D-glucose and 1 mM $CaCl_2$ and then split into two fractions. To one fraction, bovine serum albumin (BSA; fraction V, ICN) was added at 5 mg/mL (SPF-PCB+). This buffer was used for washing, loading and maintaining the cells. The BSA-free fraction was used for diluting the cells in the cuvette for measurements of fluorescence.

4. The pellet was resuspended in 10 mL of SPF-PCB+ containing 2.2 uM fluo-3 (Molecular Probes) and incubated at room temperature for 35 minutes.

5. Following the incubation period, the cells were pelleted by centrifugation. The resulting pellet was washed with SPF-PCB+. After this washing, cells were resuspended in SPF-PCB+ at a density of 1–2×106 cells/mL.

6. For recording fluorescent signals, 300 uL of cell suspension were diluted in 1.2 mL of SPF buffer containing 1 mM $CaCl_2$ and 1 mg/mL of D-glucose. Measurements of fluorescence were performed at 37° C. with constant stirring using a spectrofluorimeter. Excitation and emission wavelengths were measured at 485 and 535 nm, respectively. To calibrate fluorescence signals, digitonin (5 mg/mL in ethanol) was added to obtain Fmax, and the apparent Fmin was determined by adding Tris-EGTA (2.5 M Tris-Base, 0.3 M EGTA). The concentration of intracellular calcium was calculated using the following equation: Intracellular calcium=$(F-F_{min}/F_{max})\times K_d$; where $K_d$=400 nM.

7. To determine the potential calcilytic activity of test compounds, cells were incubated with test compound (or vehicle as a control) for 90 seconds before increasing the concentration of extracellular $Ca^{2+}$ from 1 to 2 mM. Calcilytic compounds were detected by their ability to block, in a concentration-dependent manner, increases in the concentration of intracellular $Ca^{2+}$ elicited by extracellular $Ca^{2+}$.

In general, those compounds having lower $IC_{50}$ values in the Calcium Receptor Inhibitor Assay are more preferred compounds. Compounds having an $IC_{50}$ greater than 50 uM were considered to be inactive. Preferred compounds are those having an $IC_{50}$ Of 10 uM or lower, more preferred compounds have an $IC_{50}$ of 1 uM, and most preferred compounds have an $IC_{50}$ of 0.1 uM or lower.

(II) Calcium Receptor Binding Assay

HEK 293 4.0–7 cells stably transfected with the Human Parathyroid Calcium Receptor ("HuPCaR") were scaled up in T180 tissue culture flasks. Plasma membrane is obtained by polytron homogenization or glass douncing in buffer (50 mM Tris-HCl pH 7.4, 1 mM EDTA, 3 mM $MgCl_2$) in the presence of a protease inhibitor cocktail containing 1 uM Leupeptin, 0.04 uM Pepstatin, and 1 mM PMSF. Aliquoted membrane was snap frozen and stored at −80° C. $^3H$ labeled compound was radiolabeled to a radiospecific activity of 44 Ci/mmole and was aliquoted and stored in liquid nitrogen for radiochemical stability.

A typical reaction mixture contains 2 nM $^3H$ compound ((R,R)-N-4'-Methoxy-t-3-3'-methyl-1'-ethylphenyl-1-(1-naphthyl)ethylamine), or $^3H$ compound (R)-N-[2-Hydroxy-3-(3-chloro-2-cyanophenoxy)propyl]-1,1-dimethyl-2-(4-methoxyphenyl)ethylamine 4–10 ug membrane in homogenization buffer containing 0.1% gelatin and 10% EtOH in a reaction volume of 0.5 mL. Incubation is performed in 12×75 polyethylene tubes in an ice water bath. To each tube 25 uL of test sample in 100% EtOH is added, followed by 400 uL of cold incubation buffer, and 25 uL of 40 nM $^3H$-compound in 100% EtOH for a final concentration of 2 nM. The binding reaction is initiated by the addition of 50 uL of 80–200 ug/mL HEK 293 4.0–7 membrane diluted in incubation buffer, and allowed to incubate at 4° C. for 30 min. Wash buffer is 50 mM Tris-HCl containing 0.1% PEI. Nonspecific binding is determined by the addition of 100-fold excess of unlabeled homologous ligand, and is generally 20% of total binding. The binding reaction is terminated by rapid filtration onto 1% PEI pretreated GF/C filters using a Brandel Harvestor. Filters are placed in scintillation fluid and radioactivity assessed by liquid scintillation counting.

EXAMPLES

Nuclear magnetic resonance spectra were recorded at either 250 or 400 MHz using, respectively, a Bruker AM 250 or Bruker AC 400 spectrometer. $CDCl_3$ is deuteriochloroform, DMSO-$d_6$ is hexadeuteriodimethylsulfoxide, and $CD_3OD$ is tetradeuteriomethanol. Chemical shifts are reported in parts per million (●) downfield from the internal standard tetramethylsilane. Abbreviations for NMR data are as follows: s=singlet, d=doublet, t=triplet, q=quartet, m=multiplet, dd=doublet of doublets, dt=doublet of triplets, app=apparent, br=broad. J indicates the NMR coupling constant measured in Hertz. Continuous wave infrared (IR) spectra were recorded on a Perkin-Elmer 683 infrared spectrometer, and Fourier transform infrared (FTIR) spectra were recorded on a Nicolet Impact 400 D infrared spectrometer. IR and FTIR spectra were recorded in transmission mode, and band positions are reported in inverse wavenumbers ($cm^{-1}$). Mass spectra were taken on either VG 70 FE, PE Syx API III, or VG ZAB HF instruments, using fast atom bombardment (FAB) or electrospray (ES) ionization techniques. Elemental analyses were obtained using a Perkin-Elmer 240C elemental analyzer. Melting points were taken on a Thomas-Hoover melting point apparatus and are uncorrected. All temperatures are reported in degrees Celsius.

Analtech Silica Gel GF and E. Merck Silica Gel 60 F-254 thin layer plates were used for thin layer chromatography. Both flash and gravity chromatography were carried out on E. Merck Kieselgel 60 (230–400 mesh) silica gel. Analytical and preparative HPLC were carried out on Rainin or Beckman chromatographs. ODS refers to an octadecylsilyl derivatized silica gel chromatographic support. 5μ Apex-ODS indicates an octadecylsilyl derivatized silica gel chromatographic support having a nominal particle size of 5μ, made by Jones Chromatography, Littleton, Colo. YMC ODS-AQ® is an ODS chromatographic support and is a registered trademark of YMC Co. Ltd., Kyoto, Japan. PRP-1® is a polymeric (styrene-divinylbenzene) chromatographic support, and is a registered trademark of Hamilton Co., Reno, Nev.) Celite® is a filter aid composed of acid-washed diatomaceous silica, and is a registered trademark of Manville Corp., Denver, Colo. Following the general procedure described above the following compounds have been synthesized:

Example 1

Preparation of N-[(2R)-Hydroxy-3-[[2-cyano-5-[[5-carboxyl]-3-pyridyl]phenoxy]propyl]]-1,1-dimethyl-2-(5-chlorothienyl)ethylamine a) 5-(4-Cyano-3-fluoro-phenyl)-nicotinic acid ethyl ester A solution of 2-fluoro-4-bromobenzonitrile in DMF is treated with potassium acetate, bispinacolatoboronate (1.1 equiv.) and catalytic $PdCl_2(dppf)$ and heated for 2 h at 80° C. The reaction mixture is cooled to room temperature and 4-bromonicotinic acid (1 equiv.) is added along with fresh catalyst and 2 M $Na_2CO_3$ and the resulting mixture is stirred at 80° C. for 18 h. Solvent is removed and the residue is treated with 4N HCl/dioxane in refluxing ethanol for 18 h. The reaction is evaporated and the residue in ethyl acetate is washed with NaHCO$_3$ (aqueous), dried over MgSO$_4$ and evaporated to give 5-(4-cyano-3-fluoro-phenyl)-nicotinic acid ethyl ester.

b) 5-(4-Cyano-3-hydroxy-phenyl)-nicotinic acid ethyl ester

A mixture of 5-(4-cyano-3-fluoro-phenyl)-nicotinic acid ethyl ester from Example 1a, potassium acetate (2 equiv.), and 18-crown-6 ether (2 equiv.) in MeCN is heated at reflux in 36 h. The mixture is cooled, aqueous sodium carbonate is added and stirred at room temperature overnight. The mixture was extracted with ether (discarded). The aqueous layer is neutralized with 1N HCl, extracted with EtOAc, dried over MgSO$_4$, and concentrated. Purification by flash column chromatography gives 5-(4-cyano-3-hydroxy-phenyl)-nicotinic acid ethyl ester.

c) 5-(4-Cyano-3-R-oxiranylmethoxy-phenyl)-nicotinic acid ethyl ester

A mixture of the 5-(4-cyano-3-hydroxy-phenyl)-nicotinic acid ethyl ester from Example 1b (1 equiv.), potassium carbonate (2 equiv.), and R-glycidyl-3-nitrobenzenesulfonate (1 equiv.) in acetone is heated at reflux in 24 h. The mixture is cooled, concentrated, taken up in H$_2$O and is extracted with ethyl acetate. The organic extracts are washed with brine, dried over MgSO$_4$, concentrated to afford 5-(4-cyano-3-R-oxiranylmethoxy-phenyl)-nicotinic acid ethyl ester.

d) N-[(2R)-Hydroxy-3-[[2-cyano-5-[[5-carboxyl]-3-pyridyl]phenoxy]propyl]]1,1-dimethyl-2-(5-chlorothienyl) ethylamine A mixture of 5-(4-cyano-3-R-oxiranylmethoxy-phenyl)-nicotinic acid ethyl ester from Example 1c (1 equiv.), lithium perchlorate (1 equiv.), and 1,1-dimethyl-2-(5-chlorothienyl) ethylamine (1.1 equiv.) in dioxane is heated at reflux for 48 h. The mixture is cooled, concentrated, taken up in H$_2$O, extracted with CH$_2$Cl$_2$. The organic extracts are washed with brine, dried over MgSO$_4$, concentrated, and purified by flash column chromatography to afford N-[(2R)-hydroxy-3-[[2-cyano-5-[[5-carboxyl]-3-pyridyl]phenoxy]propyl]]-1,1-dimethyl-2-(5-chlorothienyl)ethylamine.

Example 2

Preparation of N-[(2R)-Hydroxy-3-[[2-cyano-5-[[5-carboxyl]-3-pyridyl]phenoxy]propyl]]-1,1-dimethyl-2-(5-chlorothienyl)ethylamine To a stirred solution of the compound from Example 1d in dioxane is added 2.5N NaOH (aqueous). The resulting solution is stirred at room temperature for 18 h. The mixture is concentrated, taken up in H$_2$O, acidified with 2N HCl to pH=4 to give N-[(2R)-hydroxy-3-[[2-cyano-5-[[5-carboxyl]-3-pyridyl]phenoxy]propyl]]-1,1-dimethyl-2-(5-chlorothienyl)ethylamine as its bis-hydrochloride salt.

Example 3

Preparation of N-[(2R)-Hydroxy-3-[[2-cyano-5-[[5-ethylcarboxyl]-3-pyridyl]phenoxy]propyl]]-1,1-dimethyl-2-(indan-2-yl)ethylamine A mixture of the compound from Example 1c (1 equiv.), lithium perchlorate (1 equiv.), and 1,1-dimethyl-2-(indan-2-yl)ethylamine (1.1 equiv.) in dioxane is heated at reflux for 48 h. The mixture is cooled, concentrated, taken up in H$_2$O, extracted with CH$_2$Cl$_2$. The organic extracts are washed with brine, dried over MgSO$_4$, concentrated, and purified by flash column chromatography to N-[(2R)-hydroxy-3-[[2-cyano-5-[[5-ethylcarboxyl]-3-pyridyl]phenoxy]propyl]]-1,1-dimethyl-2-(indan-2-yl)ethylamine.

Example 4

Preparation of N-[(2R)-Hydroxy-3-[[2-cyano-5-[[5-carboxyl]-3-pyridyl]phenoxy]propyl]]-1,1-dimethyl-2-(indan-2-yl)ethylamine To a stirred solution of the compound from Example 3 in dioxane is added 2.5N NaOH (aqueous). The resulting solution is stirred at room temperature for 18 h. The mixture is concentrated, taken up in H$_2$O, acidified with 2N HCl to pH=4 to give N-[(2R)-hydroxy-3-[[2-cyano-5-[[5-carboxyl]-3-pyridyl]phenoxy]propyl]]-1,1-dimethyl-2-(indan-2-yl)ethylamine.

Example 5

Preparation of N-[(2R)-Hydroxy-3-[[2-cyano-5-[[5-ethylcarboxyl]-3-pyridyl]phenoxy]propyl]]-1,1-dimethyl-4-(methoxyphenyl)ethylamine A mixture of Example 1c (1 equiv.), lithium perchlorate (1 equiv.), and 1,1-dimethyl-4-(methoxyphenyl)ethylamine (1.1 equiv.) in dioxane is heated at reflux for 48 h. The mixture is cooled, concentrated, taken up in H$_2$O, extracted with CH$_2$Cl$_2$. The organic extracts are washed with brine, dried over MgSO$_4$, concentrated, purified by flash column chromatography to afford N-[(2R)-hydroxy-3-[[2-cyano-5-[[5-ethylcarboxyl]-3-pyridyl]phenoxy]propyl]]-1,1-dimethyl-4-(methoxyphenyl)ethylamine.

Example 6

Preparation of N-[(2R)-Hydroxy-3-[[2-cyano-5-[[5-carboxyl]-3-pyridyl]phenoxy]propyl]]-1,1-dimethyl-4-(methoxyphenyl)ethylamine To a stirred solution of the compound from Example 5 in dioxane is added 2.5N NaOH (aqueous), and is stirred at room temperature for 18 h. The mixture is concentrated, taken up in H$_2$O, acidified with 2N HCl to pH=4 to give N-[(2R)-hydroxy-3-[[2-cyano-5-[[5-carboxyl]-3-pyridyl]phenoxy]propyl]]-1,1-dimethyl-4-(methoxyphenyl)ethylamine.

Example 7

Preparation of N-[(2R)-Hydroxy-3-[[2-cyano-5-[[3-ethylcarboxyl]-2-pyridyl]phenoxy]propyl]]-1,1-dimethyl-2-(5-chlorothienyl)ethylamine a) 6-(4-Cyano-3-R-oxiranylmethoxy-phenyl)-pyridine-2-carboxylic acid ethyl ester.

Utilizing the procedure outlined in Example 1a–c but replacing 4-bromonicotinic acid with 6-bromopicolinic acid in Example 1a give 6-(4-Cyano-3-R-oxiranylmethoxy-phenyl)-pyridine-2-carboxylic acid ethyl ester.

b) N-[(2R)-Hydroxy-3-[[2-cyano-5-[[3-ethylcarboxyl]-2-pyridyl]phenoxy]propyl]]-1,1-dimethyl-2-(5-chlorothienyl) ethylamine A mixture of Example 7b (1 equiv.), lithium perchlorate (1 equiv.), and 1,1-dimethyl-2-(5-chlorothienyl)ethylamine (1.1 equiv.) in dioxane is heated at reflux for 48 h. The mixture is cooled, concentrated, taken up in H$_2$O, extracted with CH$_2$Cl$_2$. The organic extracts are washed with brine, dried over MgSO$_4$, concentrated, and purified by flash column chromatography to afford N-[(2R)-Hydroxy-3-[[2-cyano-5-[[3-ethylcarboxyl]-2-pyridyl]phenoxy]propyl]]-1,1-dimethyl-2-(5-chlorothienyl)ethylamine.

Example 8

Preparation of N-[(2R)-Hydroxy-3-[[2-cyano-5-[[3-carboxyl]-2-pyridyl]phenoxy]propyl]]-1,1-dimethyl-2-(5-chlorothienyl)ethylamine To a stirred solution of the compound from Example 7b in dioxane is added 2.5N NaOH (aqueous). The resulting solution is stirred at room temperature for 18 h. The mixture is concentrated, taken up in $H_2O$, acidified with 2N HCl to pH=4 to give N-[(2R)-Hydroxy-3-[[2-cyano-5-[[3-carboxyl]-2-pyridyl]phenoxy]propyl]]-1,1-dimethyl-2-(5-chlorothienyl)ethylamine as its bis-hydrochloride salt.

Example 9

Preparation of N-[(2R)-Hydroxy-3-[[2-cyano-5-[[3-ethylcarboxyl]-2-pyridyl]phenoxy]propyl]]-1,1-dimethyl-2-(indan-2-yl)ethylamine A mixture of Example 7b (1 equiv.), lithium perchlorate (1 equiv.), and 1,1-dimethyl-2-(indan-2-yl)ethylamine (1.1 equiv.) in dioxane is heated at reflux for 48 h. The mixture is cooled, concentrated, taken up in $H_2O$, extracted with $CH_2Cl_2$. The organic extracts are washed with brine, dried over $MgSO_4$, concentrated, and purified by flash column chromatography to afford N-[(2R)-hydroxy-3-[[2-cyano-5-[[3-ethylcarboxyl]-2-pyridyl]phenoxy]propyl]]-1,1-dimethyl-2-(indan-2-yl)ethylamine.

Example 10

Preparation of N-[(2R)-Hydroxy-3-[[2-cyano-5-[[3-carboxyl]-2-pyridyl]phenoxy]propyl]]-1,1-dimethyl-2-(indan-2-yl)ethylamine To a stirred solution of the compound from Example 9 in dioxane is added 2.5N NaOH (aqueous). The resulting solution is stirred at room temperature for 18 h. The mixture is concentrated, taken up in $H_2O$, acidified with 2N HCl to pH=4 to give N-[(2R)-hydroxy-3-[[2-cyano-5-[[3-carboxyl]-2-pyridyl]phenoxy]propyl]]-1,1-dimethyl-2-(indan-2-yl)ethylamine.

Example 11

Preparation of N-[(2R)-Hydroxy-3-[[2-cyano-5-[[3-ethylcarboxyl]-2-pyridyl]phenoxy]propyl]]-1,1-dimethyl-4-(methoxyphenyl)ethylamine A mixture of Example 7b (1 equiv.), lithium perchlorate (1 equiv.), and 1,1-dimethyl-4-(methoxyphenyl)ethylamine (1.1 equiv.) in dioxane is heated at reflux for 48 h. The mixture is cooled, concentrated, taken up in $H_2O$, extracted with $CH_2Cl_2$. The organic extracts are washed with brine, dried over $MgSO_4$, concentrated, and purified by flash column chromatography to afford N-[(2R)-hydroxy-3-[[2-cyano-5-[[3-ethylcarboxyl]-2-pyridyl]phenoxy]propyl]]-1,1-dimethyl-4-(methoxyphenyl)ethylamine.

Example 12

Preparation of N-[(2R)-Hydroxy-3-[[2-cyano-5-[[3-carboxyl]-2-pyridyl]phenoxy]propyl]]-1,1-dimethyl-4-(methoxyphenyl)ethylamine To a stirred solution of the compound from Example 11 in dioxane is added 2.5N NaOH (aqueous). The resulting solution is stirred at room temperature for 18 h. The mixture is concentrated, taken up in $H_2O$, acidified with 2N HCl to pH=4 to give N-[(2R)-hydroxy-3-[[2-cyano-5-[[3-carboxyl]-2-pyridyl]phenoxy]propyl]]-1,1-dimethyl-4-(methoxyphenyl)ethylamine.

Example 13

Preparation of N-[(2R)-Hydroxy-3-[[2-cyano-4-[[4-ethylcarboxyl]phenyl]-3-pyridyloxy]propyl]]-1,1-dimethyl-2-(5-chlorothienyl)ethylamine a) 2-Bromo-3-methoxy-pyridine A solution of 2-bromo-3-hydroxy-pyridine (1 equiv., Aldrich Chemical Company) in THF is treated with NaH (1 equiv.) at 0° C. for 30 min. Methyl iodide (1 equiv.) is added and stirred for 18 h. The reaction mixture is evaporated, the residue is taken into ethyl acetate, washed with 5% $Na_2CO_3$ (aqueous), dried over $MgSO_4$ and evaporated to give 2-bromo-3-methoxy-pyridine.

b) 3-Methoxy-pyridine-2-carbonitrile

A solution of 2-bromo-3-methoxy-pyridine from Example 13a in DMSO is treated with NaCN at 120° C. for 18 h. The reaction mixture is evaporated, the residue is taken into ethyl acetate, washed with 5% $Na_2CO_3$ (aqueous), dried over $MgSO_4$ and evaporated to give 3-methoxy-pyridine-2-carbonitrile.

c) 6-Bromo-3-methoxy-pyridine-2-carbonitrile

A solution of 3-methoxy-pyridine-2-carbonitrile from Example 13b in $CCl_4$ is treated with N-bromosuccinimide (1 equiv.) and catalytic 2,2-azobisisobutyronitrile and is heated at reflux for 18 h. The reaction mixture is evaporated, the residue is taken into ethyl acetate, washed with 5% $Na_2CO_3$ (aqueous), 5% $Na_2S_2O_3$ (aqueous), dried over $MgSO_4$ and evaporated to give 6-bromo-3-methoxy-pyridine-2-carbonitrile.

d) 4-(6-Cyano-5-methoxy-pyridin-2-yl)-benzoic acid ethyl ester

A solution of 6-bromo-3-methoxy-pyridine-2-carbonitrile from Example 13c in toluene is treated with 2 M $Na_2CO_3$ (aqueous), 4-carboxylphenylboronic acid (1 equiv.), ethanol and catalytic $(Ph_3P)_4Pd)$ and is heated at 80° C. for 18 h. The reaction mixture is evaporated and the residue is dissolved in ethanol with 4 N HCl in dioxane and heated at reflux for 18 h. The reaction mixture is evaporated, the residue taken into ethyl acetate, washed with 5% $Na_2CO_3$ (aqueous), dried over $MgSO_4$ and evaporated to give 4-(6-cyano-5-methoxy-pyridin-2-yl)-benzoic acid ethyl ester.

e) 4-(6-Cyano-5-hydroxy-pyridin-2-yl)-benzoic acid ethyl ester

A solution of 4-(6-cyano-5-methoxy-pyridin-2-yl)-benzoic acid ethyl ester from Example 13d in collidine is treated with LiI and heated at 120° C. for 24 h. The reaction mixture is evaporated, the residue is taken into water and neutralized with 1 N HCl. The resulting precipitate is collected and dried to give 4-(6-cyano-5-hydroxy-pyridin-2-yl)-benzoic acid ethyl ester.

f) 4-(6-Cyano-5-oxiranylmethoxy-pyridin-2-yl)-benzoic acid ethyl ester

A mixture of the compound from Example 13e (1 equiv.), potassium carbonate (2 equiv.), and R-glycidyl-3-nitrobenzenesulfonate (1 equiv.) in acetone is heated at reflux in 24 h. The mixture was cooled, concentrated, is taken up in $H_2O$ and is extracted with ethyl acetate. The organic extracts are washed with brine, dried over $MgSO_4$, and concentrated to afford 4-(6-cyano-5-oxiranylmethoxy-pyridin-2-yl)-benzoic acid ethyl ester.

g) N-[(2R)-Hydroxy-3-[[2-cyano-4-[[4-ethylcarboxyl]phenyl]-3-pyridyloxy]propyl]]-1,1-dimethyl-2-(5-chlorothienyl)ethylamine A mixture of Example 13f (1 equiv.), lithium perchlorate (1 equiv.), and 1,1-dimethyl-2-(5-chlorothienyl)ethylamine

17

(1.1 equiv.) in dioxane is heated at reflux in 48 h. The mixture is cooled, concentrated, taken up in H₂O, extracted with CH₂Cl₂. The organic extracts are washed with brine, dried over MgSO₄, concentrated and purified by flash column chromatography to afford N-[(2R)-hydroxy-3-[[2-cyano-4-[[4-ethylcarboxyl]phenyl]-3-pyridyloxy]propyl]]-1,1-dimethyl-2-(5-chlorothienyl)ethylamine.

Example 14

Preparation of N-[(2R)-Hydroxy-3-[[2-cyano-4-[[4-carboxyl]phenyl]-3-pyridyloxy]propyl]]-1,1-dimethyl-2-(5-chlorothienyl)ethylamine To a stirred solution of the compound from Example 13g in dioxane is added 2.5N NaOH (aqueous), and is stirred at room temperature for 18 h. The mixture is concentrated, taken up in H₂O, acidified with 2N HCl to pH=4 to give N-[(2R)-hydroxy-3-[[2-cyano-4-[[4-carboxyl]phenyl]-3-pyridyloxy]propyl]]-1,1-dimethyl-2-(5-chlorothienyl)ethylamine.

Example 15

Preparation of N-[(2R)-Hydroxy-3-[[2-cyano-4-[[4-ethylcarboxyl]phenyl]-3-pyridyloxy]propyl]]-1,1-dimethyl-2-(indan-2-yl)ethylamine A mixture of Example 13e (1 equiv.), lithium perchlorate (1 equiv.), and 1,1-dimethyl-2-(indan-2-yl)ethylamine (1.1 equiv.) in dioxane is heated at reflux for 48 h. The mixture is cooled, concentrated, taken up in H₂O, extracted with CH₂Cl₂. The organic extracts are washed with brine, dried over MgSO₄, concentrated, purified by flash column chromatography to afford N-[(2R)-hydroxy-3-[[2-cyano-4-[[4-ethylcarboxyl]phenyl]-3-pyridyloxy]propyl]]-1,1-dimethyl-2-(indan-2-yl)ethylamine,.

Example 16

Preparation of N-[(2R)-Hydroxy-3-[[2-cyano-4-[[4-carboxyl]phenyl]-3-pyridyloxy]]-1,1-dimethyl-2-(indan-2-yl)ethylamine To a stirred solution of the compound from Example 15 in dioxane is added 2.5N NaOH (aqueous). The resulting solution is stirred at room temperature for 18 h. The mixture is concentrated, taken up in H₂O, acidified with 2N HCl to pH=4 to give N-[(2R)-hydroxy-3-[[2-cyano-4-[[4-carboxyl]phenyl]-3-pyridyloxy]]-1,1-dimethyl-2-(indan-2-yl)ethylamine.

Example 17

Preparation of N-[(2R)-Hydroxy-3-[[2-cyano-4-[[4-ethylcarboxyl]phenyl]-3-pyridyloxy]propyl]]-1,1-dimethyl-4-(methoxyphenyl)ethylamine A mixture of Example 13e (1 equiv.), lithium perchlorate (1 equiv.), and 1,1-dimethyl-4-(methoxyphenyl)ethylamine (1.1 equiv.) in dioxane is heated at reflux for 48 h. The mixture is cooled, concentrated, taken up in H₂O, extracted with CH₂Cl₂. The organic extracts are washed with brine, dried over MgSO₄, concentrated, purified by flash column chromatography to afford N-[(2R)-hydroxy-3-[[2-cyano-4-[[4-ethylcarboxyl]phenyl]-3-pyridyloxy]propyl]]-1,1-dimethyl-4-(methoxyphenyl)ethylamine.

Example 18

Preparation of N-[(2R)-Hydroxy-3-[[2-cyano-4-[[4-carboxyl]phenyl]-3-pyridyloxy]propyl]]-1,1-dimethyl-4-(methoxyphenyl)ethylamine To a stirred solution of the compound from Example 5 in dioxane is added 2.5N NaOH (aqueous). The resulting solution is stirred at room temperature for 18 h. The mixture is concentrated, taken up in H₂O, acidified with 2N HCl to pH=4 to give N-[(2R)-hydroxy-3-[[2-cyano-4-[[4-carboxyl]phenyl]-3-pyridyloxy]propyl]]-1,1-dimethyl-4-(methoxyphenyl)ethylamine.

Example 19

Parenteral Formulation

A pharmaceutical composition for parenteral administration is prepared by dissolving an appropriate amount of a compound of Formula (I) in polyethylene glycol with heating. This solution is then diluted with water for injections (to 100 ml). The solution is then rendered sterile by filtration through a 0.22 micron membrane filter and sealed in sterile containers.

All publications, including but not limited to patents and patent applications cited in this specification are herein incorporated by reference as if each individual publication were specifically and individually indicated to be incorporated by reference as though fully set forth.

What is claimed is:

1. A compound selected from the group consisting of:
   N-[(2R)-Hydroxy-3-[[2-cyano-5-[[5-ethylcarboxyl]-3-pyridyl]phenoxy]propyl]]-1,1-dimethyl-2-(5-chlorothienyl)ethylamine;

N-[(2R)-Hydroxy-3-[[2-cyano-5-[[5-carboxyl]-3-pyridyl]phenoxy]propyl]]-1,1-dimethyl-2-(5-chlorothienyl)ethylamine;

N-[(2R)-Hydroxy-3-[[2-cyano-5-[[5-ethylcarboxyl]-3-pyridyl]phenoxy]propyl]]-1,1-dimethyl-2-(indan-2-yl)ethylamine;

N-[(2R)-Hydroxy-3-[[2-cyano-5-[[5-carboxyl]-3-pyridyl]phenoxy]propyl]]-1,1-dimethyl-2-(indan-2-yl)ethylamine;

N-[(2R)-Hydroxy-3-[[2-cyano-5-[[5-ethylcarboxyl]-3-pyridyl]phenoxy]propyl]]-1,1-dimethyl-4-(methoxyphenyl)ethylamine;

N-[(2R)-Hydroxy-3-[[2-cyano-5-[[5-carboxyl]-3-pyridyl]phenoxy]propyl]]-1,1-dimethyl-4-(methoxyphenyl)ethylamine;

N-[(2R)-Hydroxy-3-[[2-cyano-5-[[3-ethylcarboxyl]-2-pyridyl]phenoxy]propyl]]-1,1- dimethyl-2-(5-chlorothienyl)ethylamine;

N-[(2R)-Hydroxy-3-[[2-cyano-5-[[3-carboxyl]-2-pyridyl]phenoxy]propyl]]-1,1-dimethyl-2-(5-chlorothienyl)ethylamine;

N-[(2R)-Hydroxy-3-[[2-cyano-5-[[3-ethylcarboxyl]-2-pyridyl]phenoxy]propyl]]-1,1-dimethyl-2-(indan-2-yl)ethylamine;

N-[(2R)-Hydroxy-3-[[2-cyano-5-[[3-carboxyl]-2-pyridyl]phenoxy]propyl]]-1,1-dimethyl-2-(indan-2-yl)ethylamine;

N-[(2R)-Hydroxy-3-[[2-cyano-5-[[3-ethylcarboxyl]-2-pyridyl]phenoxy]propyl]]-1,1-dimethyl-4-(methoxyphenyl)ethylamine;

N-[(2R)-Hydroxy-3-[[2-cyano-5-[[3-carboxyl]-2-pyridyl]phenoxy]propyl]]-1,1-dimethyl-4-(methoxyphenyl)ethylamine;

N-[(2R)-Hydroxy-3- [[2-cyano-4-[[4-ethylcarboxyl]phenyl]-3-pyridyloxy]propyl]]-1,1-dimethyl-2-(5-chlorothienyl)ethylamine;

N-[(2R)-Hydroxy-3-[[2-cyano-4-[[4-carboxy]phenyl]-3-pyridyloxy]propyl]]-1,1-dimethyl-2-(5-chlorothienyl)ethylamine;

N-[(2R)-Hydroxy-3-[[2-cyano-4-[[4-ethylcarboxyl]phenyl]-3-pyridyloxy]propyl]]-1,1-dimethyl-2-(indan-2-yl)ethylamine;

N-[(2R)-Hydroxy-3-[[2-cyano-4-[[4-carboxyl]phenyl]-3-pyridyloxy]]-1,1-dimethyl-2-(indan-2-yl)ethylamine;

N-[(2R)-Hydroxy-3-[[2-cyano-4-[[4-ethylcarboxyl]phenyl]-3-pyridyloxy]propyl]]-1,1-dimethyl-4-(methoxyphenyl)ethylamine;

N-[(2R)-Hydroxy-3-[[2-cyano-4-[[4-carboxyl]phenyl]-3-pyridyloxy]propyl]]-1,1-dimethyl-4-(methoxyphenyl)ethylamine.

2. A method of treating osteoporosis in a mammal comprising administering therapeutically effective amount of compound according to claim 1.

3. A method according to claim 2 wherein the compound is co-administered with an anti-resorptive agent.

4. A method according to claim 3 wherein the anti-resorptive agent is selected from the group consisting of estrogen, 1, 25 $(OH)_2$ vitamin D3, calcitonin, selective estrogen receptor modulators, vitronectin receptor antagonists, V-H+-ATPase inhibitors, src SH2 antagonists, bisphosphonates and cathepsin K inhibitors.

* * * * *